(12) United States Patent
Sugita et al.

(10) Patent No.: US 9,423,361 B2
(45) Date of Patent: Aug. 23, 2016

(54) INNER IMAGE GENERATING APPARATUS AND METHOD THEREOF

(71) Applicant: KABUSHIKI KAISHA TOSHIBA, Minato-Ku (JP)

(72) Inventors: Tsukasa Sugita, Yokohama (JP); Haruo Miyadera, Yokohama (JP); Kenichi Yoshioka, Yokohama (JP); Naoto Kume, Yokohama (JP); Kohichi Nakayama, Yokohama (JP); Yuichiro Ban, Fujisawa (JP); Yoshiji Karino, Yokohama (JP); Kyouichi Fujita, Yokohama (JP); Shigeru Odanaka, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 14/596,745

(22) Filed: Jan. 14, 2015

(65) Prior Publication Data
US 2015/0198542 A1    Jul. 16, 2015

(30) Foreign Application Priority Data
Jan. 14, 2014   (JP) .................................. 2014-004524

(51) Int. Cl.
*G01N 23/00* (2006.01)
*G01N 23/04* (2006.01)
*G01V 5/00* (2006.01)

(52) U.S. Cl.
CPC ............. *G01N 23/04* (2013.01); *G01V 5/0016* (2013.01)

(58) Field of Classification Search
None
See application file for complete search history.

(56) References Cited

U.S. PATENT DOCUMENTS

| | | | |
|---|---|---|---|
| 7,470,905 B1* | 12/2008 | Goldberg | G01T 1/2935 250/251 |
| 8,288,721 B2* | 10/2012 | Morris | G01T 1/18 250/251 |
| 2010/0265078 A1* | 10/2010 | Friedman | G01T 1/26 340/600 |
| 2011/0001046 A1* | 1/2011 | Nagamine | G01B 15/04 250/307 |

OTHER PUBLICATIONS

Miyadera, H., et al. "Imaging Fukushima Daiichi Reactors with Muons," *AIP Advances3*, 052133 (2013).

\* cited by examiner

*Primary Examiner* — Andrew Smyth
(74) *Attorney, Agent, or Firm* — Oblon, McClelland, Maier & Neustadt, L.L.P

(57) ABSTRACT

An inner image generating apparatus includes a first receiver configured to receive an inlet track information and a first passage time of a muon, a second receiver configured to receive an outlet track information and a second passage time of the muon, a displacement calculator configured to calculate a track displacement of a track of the muon based on the inlet and outlet track information, a mean energy calculator configured to calculate a mean energy of the muon based on a time-difference between the first passage and the second passage time, a data integration circuit configured to integrate multiplied data multiplying the track displacement and the mean energy on a projected plane, and an image generating circuit configured to generate an inner image of the structure by identifying a position of matter at the projected plane based on an integrated multiplied data.

4 Claims, 5 Drawing Sheets

EXAMPLE

COMPARATIVE EXAMPLE

INNER IMAGE GENERATING APPARATUS AND METHOD THEREOF

CROSS-REFERENCE TO RELATED APPLICATION

This application is based upon and claims the benefit of priority from Japanese Patent application No. 2014-004524, filed on Jan. 14, 2014, the entire content of which is incorporated herein by reference.

FIELD OF THE INVENTION

Embodiments of the present invention relate to an inner image generating technique that generates an image of an inside of a structure using cosmic radiation muons.

RELATED ART

As a conventional technique of grasping an inside of a structure, a technique is known which observes muons that arrive at the surface of the earth and sees through the inside of the structure.

The muon is a kind of secondary cosmic radiation generated when primary cosmic radiation entering the earth from outer space reacts with the atmosphere of the earth. The muon has positive or negative charge, has high mean energy of 3 to 4 GeV and therefore possesses high penetrability.

The technique of seeing through a structure using this penetrability of muons is preferably used for a large object such as a volcano or pyramid, an inside of which is hardly accessible, and is also attracting attention as a technique for accurately grasping an interior of a structure to monitor an inner situation from outside, such as an atomic power plant hardly accessible due to high radioactivity caused by an accident.

As a method of generating an inner image (imaging) of a structure using muons, various techniques are known such as a penetration method which measures attenuation of a particle flux of muons and a scattering method which measures a Coulomb multiple scattering angle of muons. Regarding the scattering method, a displacement method is also known which measures a displacement of a track using Coulomb multiple scattering.

The aforementioned penetration method detects only an outlet track of a muon after passing through the structure and measures attenuation of the particle flux. For this reason, influences of Coulomb multiple scattering when the muon penetrates the structure are not taken into consideration and this method has a problem that resolution of an imaged object is low.

On the other hand, the scattering method detects an inlet track and an outlet track of a muon and measures a scattering angle by Coulomb multiple scattering. However, since the scattering angle of Coulomb multiple scattering depends on energy of inlet particles, there is a problem that the resolution of the object estimated from the scattering angle deteriorates due to influences of a fluctuation portion of energy.

Thus, the existing methods include factors that cause the resolution to deteriorate, and it is therefore difficult to generate an image of a large-scale structure such as an atomic power plant with high resolution.

SUMMARY OF THE INVENTION

To solve the above problems, it is an object of present invention to provide techniques in which an inner image of the structure can be generated with high resolution.

An inner image generating apparatus according to an embodiment of the present invention includes a first receiver configured to receive an inlet track information and a first passage time of a muon at a first track detector provided outside of a structure a second receiver configured to receive an outlet track information and a second passage time of the muon at a second track detector provided outside of the structure at an opposite side of the first track detector a displacement calculator configured to calculate a track displacement of a track of the muon passing the structure based on the inlet track information and the outlet track information of the muon a mean energy calculator configured to calculate a mean energy of the muon based on a time-difference between the first passage time and the second passage time a data integration circuit configured to integrate multiplied data multiplying the track displacement and the mean energy of the muon on a projected plane assumed inside the structure, wherein each of the multiplied data is configured to be allocated at a corresponding position of the muon passing at the projected plane, and an image generating circuit configured to generate an inner image of the structure by identifying a position of matter at the projected plane based on an integrated multiplied data obtained at the data integration circuit.

An inner image generating method according to an embodiment of the present invention includes receiving an inlet track information and a first passage time of a muon at a first track detector provided outside of a structure receiving an outlet track information and a second passage time of the muon at a second track detector provided outside of the structure at an opposite side of the first track detector calculating a track displacement of a track of the muon passing the structure based on the inlet track information and the outlet track information of the muon calculating a mean energy of the muon based on a time-difference between the first passage time and the second passage time integrating multiplied data multiplying the track displacement and the mean energy of the muon on a projected plane assumed inside the structure, wherein each of the multiplied data is allocated at a corresponding position of the muon passing at the projected plane, and generating an inner image of the structure by identifying a position of matter at the projected plane based on the multiplied data integrated.

DESCRIPTION OF THE EMBODIMENTS

Hereinafter, an embodiment will be described with reference to the accompanying drawings.

Figure 1:
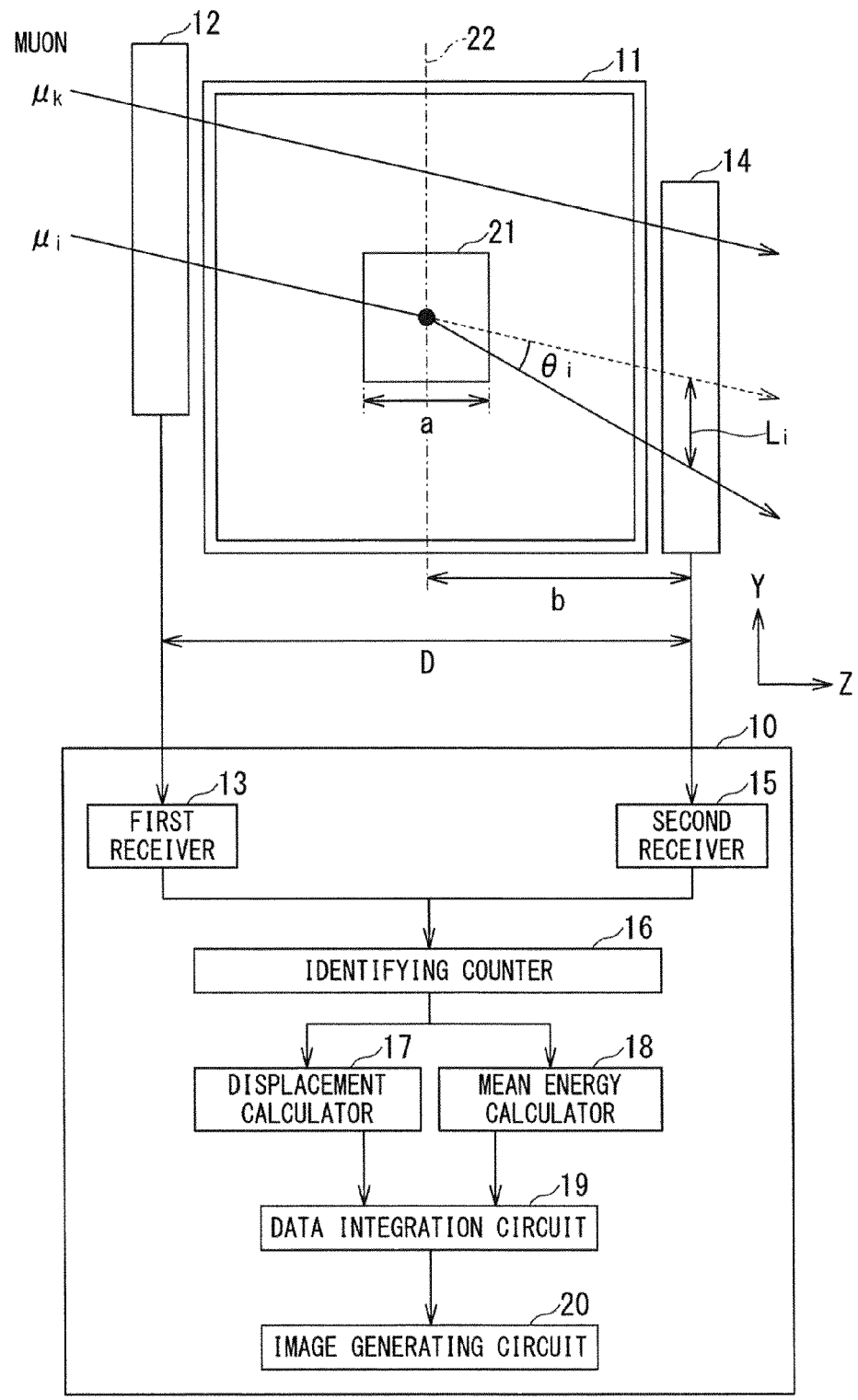
FIG. 1 is a configuration diagram of an inner image generating apparatus according to the present embodiment.

An inner image generating apparatus 10 (hereinafter referred to as "image generating apparatus 10") according to the present embodiment shown in FIG. 1 is provided with a first receiver 13 that receives inlet track information and a passage time of a muon incident on a structure 11 at a first track detector 12 provided outside of the structure 11, a second receiver 15 that receives outlet track information and a passage time of the muon having passed the structure 11 from a second track detector 14 provided outside of the structure 11 at an opposite side of the first track detector 12, a displacement calculator (track displacement calculator) 17 that calculates an estimated track estimated from the inlet track and calculates a track displacement of the muon based on the estimated track and the outlet track, a mean energy calculator 18 that calculates mean energy of the muon based on a time difference between the passage time at the first track detector 12 and the passage time at the second track detector 14, a data integration circuit 19 that integrates a product of the track displacement and the mean energy calculated for the muon on a projected plane 22 set inside the structure 11, and an image generating circuit 20 that generates an image of an inner structure 21 of the structure 11 by identifying a position of matter using the product of the track displacement and the mean energy integrated at the projected plane 22. Note that FIG. 1 illustrates flight tracks of two muons $\mu_j$ and $\mu_k$ pouring from the sky.

The first receiver 13 and the second receiver 15 making up the inner image generating apparatus 10 may be implemented not only by hardware such as an apparatus (device) that directly receives an input of a keyboard or switch, a connector that receives an input of a signal and an interface using an electronic circuit, but also by executing a predetermined program code using an electronic circuit such as a processor, or without being limited to such software processing, may be configured as a unit or computer implemented by hardware processing using an electronic circuit such as an ASIC or may be configured as a unit or computer implemented by combining software processing and hardware processing. Moreover, functions of the displacement calculator 17, mean energy calculator 18, data integration circuit 19 and image generating circuit 20 making up the inner image generating apparatus 10 may be likewise implemented by executing a predetermined program code using an electronic circuit such as a processor or without being limited to such software processing, but may be configured as a unit or computer implemented by hardware processing using an electronic circuit such as an ASIC or may be configured as a unit or computer implemented by combining software processing and hardware processing.

An imaging target of the present embodiment is, for example, the inner structure 21 (e.g., nuclear reactor container) made of heavy element matter such as uranium fuel. The inner structure 21 is housed inside of the structure 11 made of steel or concrete.

The first track detector 12 and the second track detector 14 are track detectors that detect flight tracks of muons. The track detector is configured using a scintillation detector or drift tube detector which detects passage of muon. The track detector using a drift tube detector is particularly suitable because it has high spatial resolution and angular resolution.

The first track detector 12 and the second track detector 14 are arranged at opposite positions across the structure 11.

Muons detected on the earth have angle dependency and have a greater flux as their zenith angles approximate to 0°. When intensity at a zenith angle θ is $I_v$, intensity $J_θ$ at the zenith angle θ is expressed by following Equation (1).

$$J_θ = I_v \times (\cos θ)^2 \quad \text{Equation (1)}$$

θ: Zenith angle
$I_v$: Muon intensity at zenith angle 0
$J_θ$: Muon intensity at zenith angle θ

Given this nature, the first track detector 12 and the second track detector 14 set at different heights can detect muons with greater fluxes than those set on the same horizontal level.

The first track detector 12 detects an inlet track of a muon incident upon the structure 11. The first track detector 12 then outputs detected inlet track information and a passage time of the muon to the first receiver 13.

The first receiver 13 outputs the entered inlet track and passage time at the first track detector 12 to an identifying counter 16.

On the other hand, the second track detector 14 detects an outlet track of the muon after passing through the structure 11. The second track detector 14 outputs the detected outlet track information and the passage time of the muon to the second receiver 15.

The second receiver 15 outputs the entered outlet track and passage time at the second track detector 14 to the identifying counter 16.

The identifying counter 16 sorts out inlet tracks and outlet tracks detected at the first track detector 12 and the second track detector 14 within a certain time as tracks of an identical muon. The term "certain time" means a time during which it is possible to determine that tracks are related to the identical muon and, for example, it may be a maximum time of times estimated as time necessary for the muon to pass through the structure 11.

The identifying counter 16 sorts out inlet tracks and outlet tracks associated with an identical muon from a large amount of muons detected at the first track detector 12 and the second track detector 14. Note that a configuration which omits the identifying counter 16 may be adopted if the image generating apparatus 10 limits inputs of track detection to an extent that inlet tracks and outlet tracks associated with the identical muon are sufficiently identifiable. The function of the identifying counter 16 may also be configured so as to be implemented by executing a predetermined program code using an electronic circuit such as a processor, or without being limited to such software processing, a unit or computer implemented by hardware processing using an electronic circuit such as an ASIC or may be configured as a unit or computer implemented by combining software processing and hardware processing.

Here, the projected plane 22 set inside of the structure 11 will be described.

Figure 2:
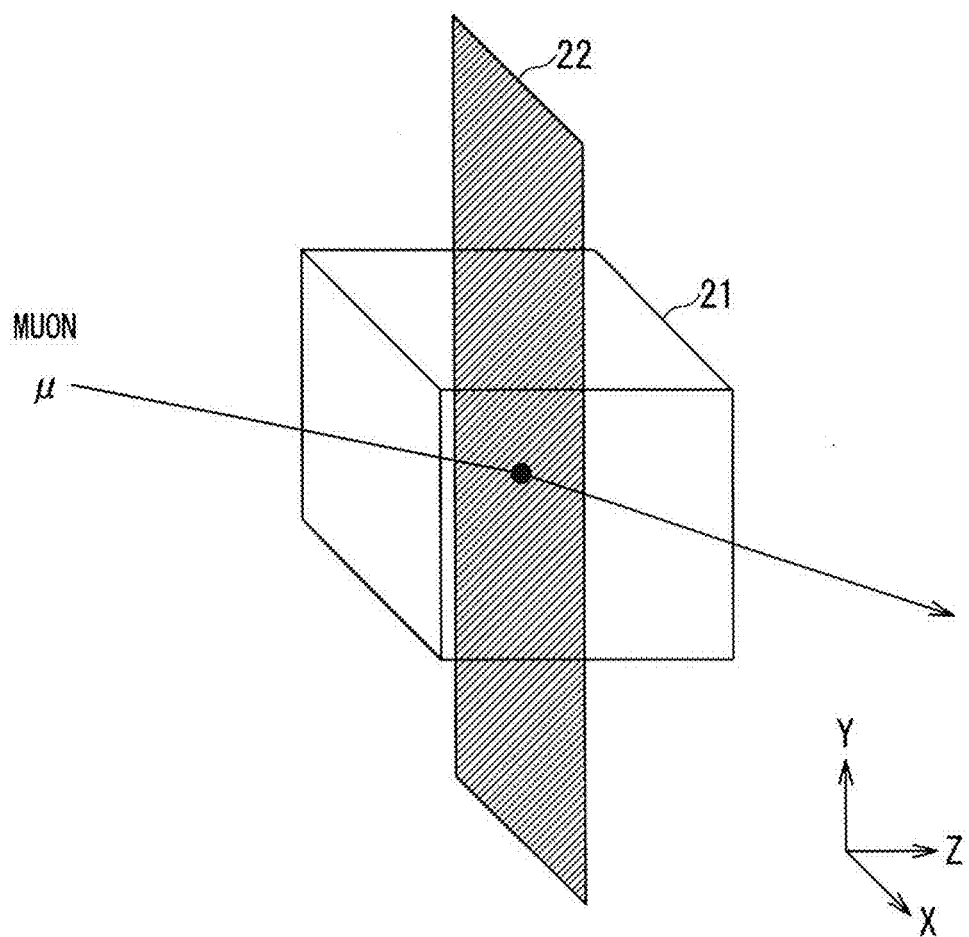
FIG. 2 is a perspective view illustrating a projected plane set inside of a structure.

The "projected plane 22" is a plane set for an analysis assumed to generate an image of a cross section of the inner structure 21 set on a plane on which the inner structure 21 is assumed to be located as shown in FIG. 2. This projected plane 22 can be set at a given position between the first track detector 12 and the second track detector 14. The projected plane 22 is preferably set to be parallel to a plane defined by at least one of the first track detector 12 and the second track detector 14.

The projected plane 22 is segmented into cells in a given size (see FIG. 3), and scattering coordinates are assigned to each cell to identify the cell.

When passing through the inner structure 21, a muon triggers Coulomb multiple scattering and is deflected due to reaction with atoms making up the inner structure 21. As a result, a track of the muon entering the structure 11 is displaced.

Here, calculation is carried out by making an approximation that Coulomb multiple scattering takes place at one point on the projected plane 22 and a point of intersection between extension of an inlet track of the muon and the projected plane 22 detected at the first track detector 12 is assumed to be a scattering point. That is, the present embodiment makes an approximation that the track of the muon passes through the scattering point on the projected plane 22.

To describe the calculation method more specifically, a muon shown in FIG. 1 will be discussed.

The displacement calculator 17 receives an inlet track and an outlet track of the muon $\mu_i$ from the identifying counter 16. The inlet track is then extended to calculate an estimated track (dotted line in the figure) estimated when the muon is not deflected.

As shown in following Equation (2), a track displacement $L_i$ of the muon $\mu_i$ in a vertical direction (height direction, y-axis direction) is derived using an angle difference $\theta_i$ (scattering angle) between the estimated track and the outlet track, and a distance b from the projected plane 22 to the second track detector 14.

$$L_i = b \times \theta_i \qquad \text{Equation (2)}$$

$L_i$: track displacement of muon $\mu_i$ [m]
b: distance [m] between projected plane and second detector
$\theta_i$: angle difference (scattering angle) between estimated track and outlet track of muon $\mu_i$ Note that deflection of a muon takes place in all matters through which the muon passes, and the greater the atomic weight of matter, the greater is the influence of the scattering angle of Coulomb multiple scattering, and therefore the heavier the heavy element matter, the greater is the value of track displacement.

On the other hand, the mean energy calculator 18 receives a passage time of the muon $\mu_i$ at each detector from the identifying counter 16. The mean energy calculator 18 then calculates mean energy of the muon $\mu_i$ based on the time difference in these passage times.

The present embodiment uses a flight time measuring method (time-of-flight method) that derives energy by measuring a flight distance and a flight time of particles as the method of measuring mean energy of flying particles.

Assuming that passage times of the muon $\mu_i$ in the first track detector 12 and the second track detector 14 are $t_1$ and $t_2$ respectively and the distance between the detectors is D, mean energy $E_i$ of the muon $\mu_i$ is derived from following Equations (3) to (5).

$$\Delta T = t_2 - t_1 \qquad \text{Equation (3)}$$

$$v = D / \Delta T \qquad \text{Equation (4)}$$

$$E_i = \frac{1}{2}mv^2 = \frac{1}{2}m\left(\frac{D}{\Delta T}\right)^2 \qquad \text{Equation (5)}$$

$t_1$: passage time [s] in first track detector of muon $\mu_i$
$t_2$: passage time [s] in second track detector of muon $\mu_i$
$\Delta T$: time difference [s]
D: distance between detectors [m]
$E_i$: mean energy [J] of muon $\mu_i$
m: mass of muon [kg]
v: flight speed of muon $\mu_i$ [m/s]

The distance D of the detection period may be measured by approximately using the distance in the horizontal direction (distance within the xz plane) between the first track detector 12 and the second track detector 14 as shown in FIG. 1.

Alternatively, the distance D may be assumed as an actual distance between the detectors such as a scintillation detector or drift tube detector that has detected passage of the muon out of the first track detector 12 and the second track detector 14.

The data integration circuit 19 receives a track displacement $L_i$ of the muon $\mu_i$ from the displacement calculator 17 and mean energy $E_i$ of the muon $\mu_i$ from the mean energy calculator 18.

The data integration circuit 19 calculates scattering coordinates (xi, yi) on the projected plane 22 corresponding to the scattering point of the muon $\mu_i$ and assigns a product (multiplied datum) of the track displacement $L_i$ and the mean energy $E_i$ to the scattering coordinates (xi, yi).

Similarly, the data integration circuit 19 receives the product of the track displacement L and the mean energy E calculated for each muon other than the muon $\mu_i$. The data integration circuit 19 then assigns this product to the scattering coordinates on the projected plane 22 and integrates the product of the track displacement L and the mean energy E on the projected plane 22. When products of the track displacements L and the mean energy E by a plurality of muons are assigned to scattering coordinates (x, y) at one certain point on the projected plane 22, integration is performed by calculating a mean value of the plurality of product values and assigning the mean value. For the mean value, various calculations such as arithmetical mean, geometrical mean can be used.

Figure 3:
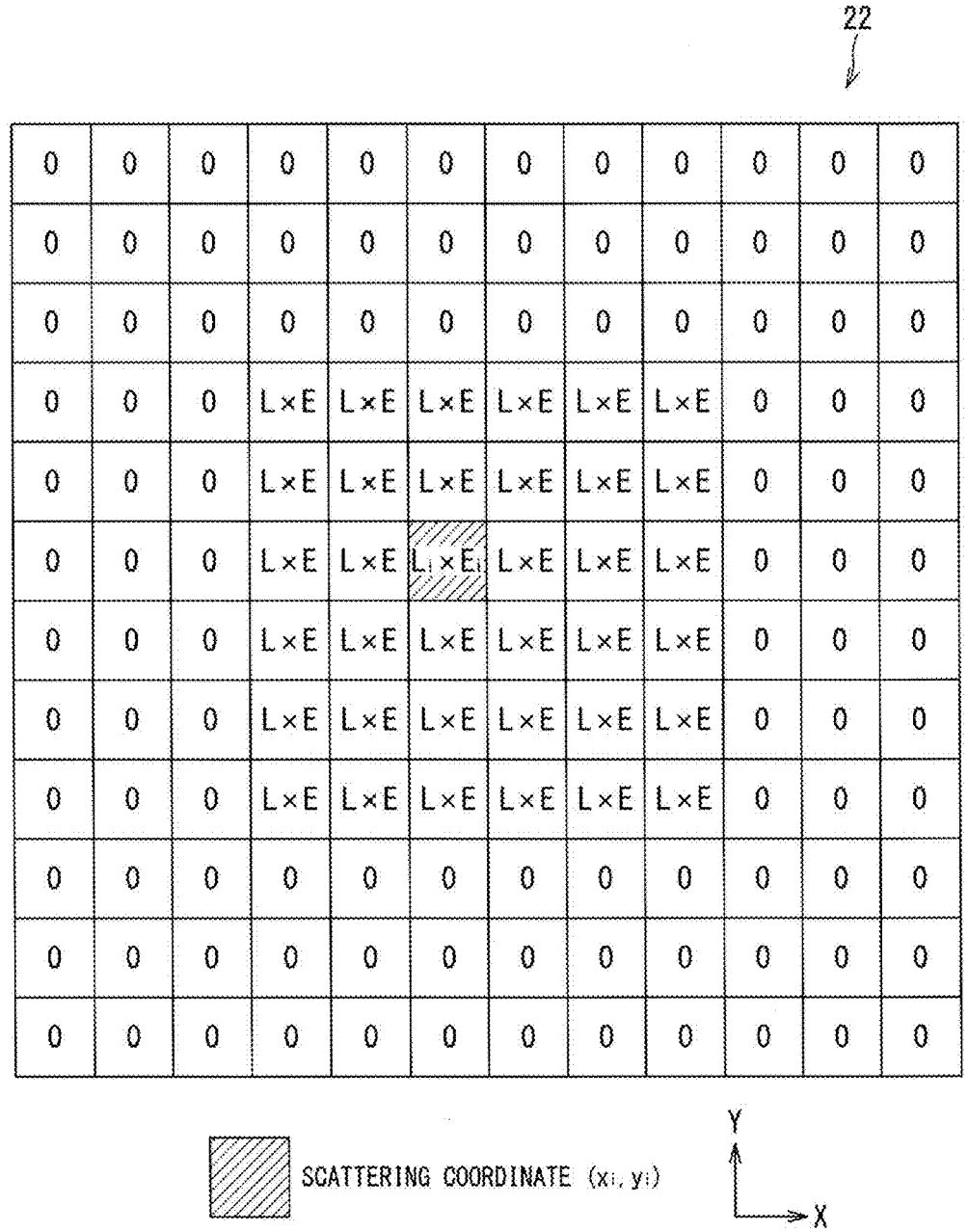
FIG. 3 is a diagram illustrating the product of a track displacement of muon and mean energy integrated on a projected plane.

FIG. 3 is a diagram illustrating the product of the track displacement and the mean energy of the muon is integrated on the projected plane 22. The product of the track displacement $L_i$ and the mean energy $E_i$ corresponding to the muon is assigned to the scattering coordinates (xi, yi). When there is no track displacement as in the case of a muon $\mu_k$ (FIG. 1), the product of the track displacement L and the mean energy E becomes 0, and therefore 0 is assigned to the scattering coordinates. As described above, when the product of the track displacement L and the mean energy E by a plurality of muons is assigned to scattering coordinates at one location on the projected plane 22, a mean value of the plurality of product values is assigned.

The product of the track displacement and mean energy of a muon is expressed as a function of a thickness and radiation length specific to matter of the inner structure 21 through which the muon passes as shown in following Equation (6).

[Formula 1]

$$L \times E \propto \sqrt{\frac{a}{X_0}} \qquad \text{Equation (6)}$$

L: track displacement of muon [m]
E: mean energy of muon [J]
a: thickness of inner structure [m]
$X_0$: radiation length [m]

The radiation length $X_0$ refers to a mean distance that a particle travels until energy is reduced to 1/e while passing through the matter, which is a value specific to each matter. The radiation length is a function of an atomic number Z as shown in following Equation (7).

[Formula 2]

$$X_0 = \frac{7.164 \cdot A}{dZ(Z+1)\ln\frac{287}{\sqrt{Z}}}$$ Equation (7)

$X_0$: radiation length [m]
d: density [g·cm$^{-3}$]
A: atomic mass number
Z: atomic number It is seen from Equation (7) that the radiation length is inversely proportional to Z. The radiation length of typical matter such as water, concrete, iron or uranium is approximately $3.93 \times 10^{-1}$, $11.6 \times 10^{-1}$, $1.76 \times 10^{-2}$, $3.17 \times 10^{-3}$ m respectively.

Therefore, the product of the track displacement L and the mean energy E has a feature of taking on a greater numerical value at a position where a heavy element exists and taking on a smaller value at a position where no matter exists or a light element exists.

Taking advantage of this feature, the image generating circuit 20 identifies the position of existence of matter from the product of the track displacement L and the mean energy E integrated on the projected plane 22 and generates an image of the inner structure 21.

When a thickness a of the inner structure 21 is known, it is possible to identify the atomic number of matter from the product of the track displacement L and the mean energy E using aforementioned Equation (6) and Equation (7). The image generating circuit 20 identifies the atomic number from the product of the track displacement L and the mean energy E, causes this identification information to be reflected and can thereby generate an image of the inner structure 21.

Thus, by identifying the position of existence of matter from two components of the track displacement and the mean energy, the position resolution improves compared to a case where an image is generated using only the track displacement, and an image of the interior of the structure 11 can thereby be generated with a high resolution.

In FIG. 1, the projected plane 22 is set at the center position of the inner structure 21, but by continuously changing the projected plane 22, it is also possible to acquire a three-dimensional tomographic image.

Figure 4:
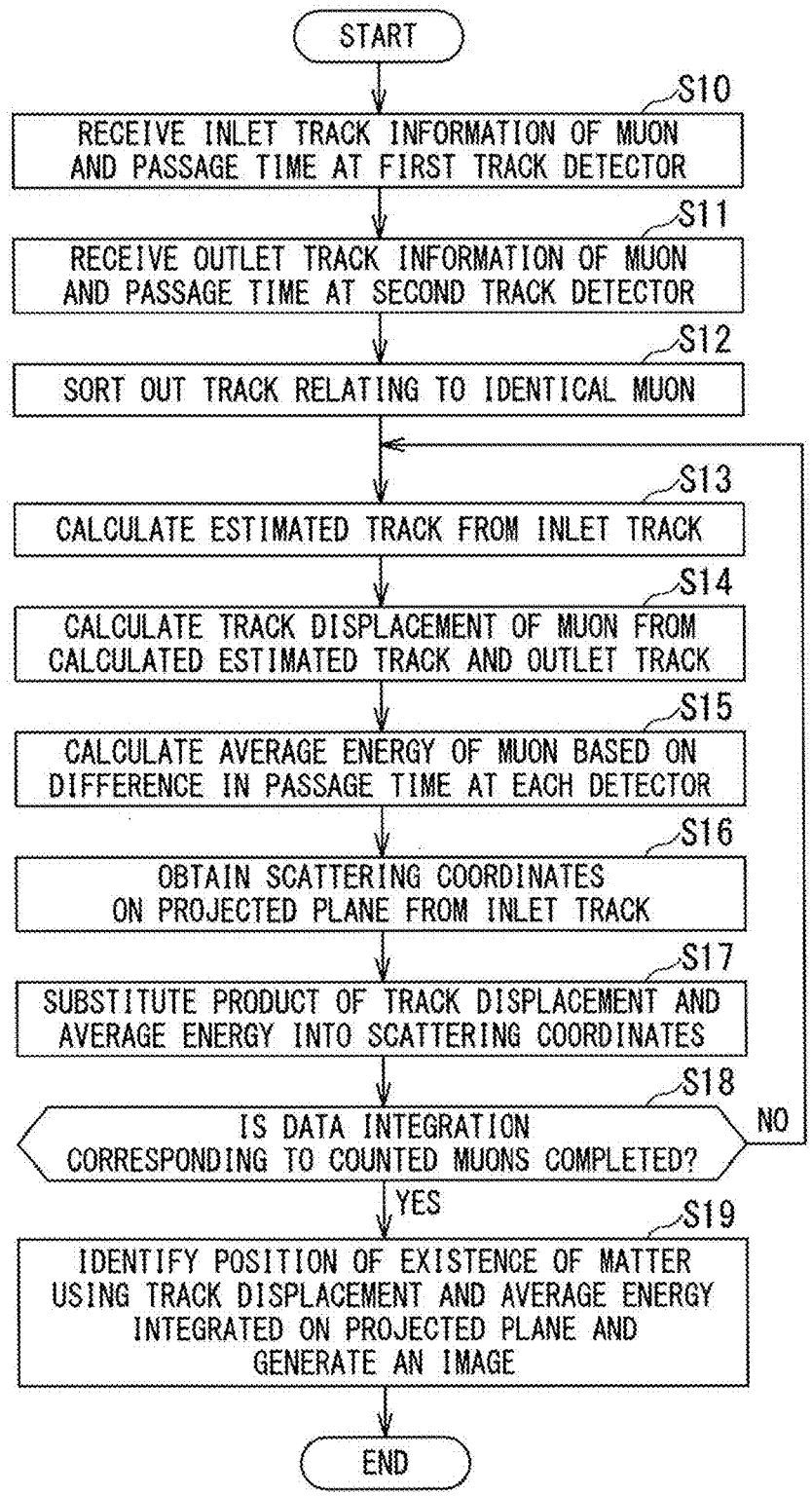
FIG. 4 is a flowchart illustrating operation of the inner image generating apparatus according to the present embodiment.

FIG. 4 is a flowchart illustrating operation of the inner image generating apparatus 10 (see FIG. 1 as appropriate).

The first receiver 13 receives inlet track information and a passage time of a muon at the first track detector 12 from the first track detector 12 (S10).

The second receiver 15 receives outlet track information and a passage time of the muon at the second track detector 14 from the second track detector 14 (S11).

The identifying counter 16 sorts out an inlet track and an outlet track detected within a certain period of time as a track related to an identical muon (S12).

The displacement calculator 17 calculates an estimated track from the inlet track and calculates a track displacement of the muon from the estimated track and outlet track (S13, S14).

The mean energy calculator 18 calculates mean energy of the muon based on a time difference in the passage time at each detector (S15).

The data integration circuit 19 obtains scattering coordinates on the projected plane from the inlet track (S16). The data integration circuit 19 then assigns the product of the track displacement and the mean energy to the scattering coordinates (S17).

The data integration circuit 19 repeats assignment of the product of the track displacement and the mean energy to the scattering coordinates by the number of muons counted (the number of inlet muons) and integrates the products on the projected plane 22 (S18: NO, S13 to S17).

When data integration is completed, the image generating circuit 20 identifies the position of existence of matter using the track displacement and mean energy integrated on the projected plane 22 and generates an image (S18: YES, S19).

Figure 5A:
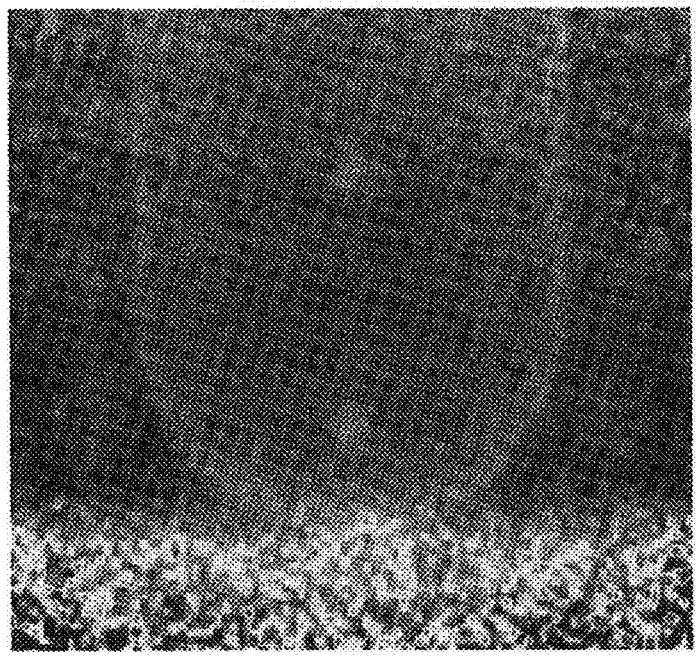
FIG. 5A shows a simulation result when an inner image of a nuclear reactor is generated according to the present embodiment.
Figure 5B:
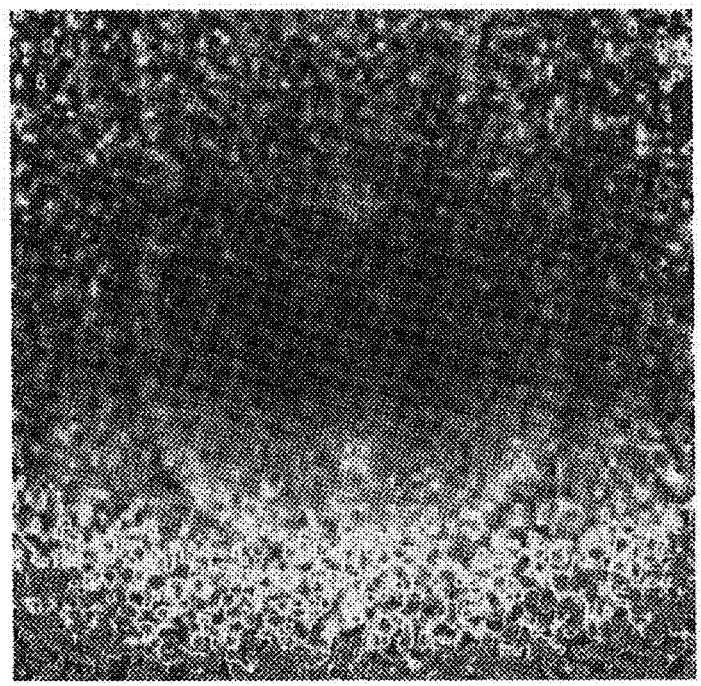
FIG. 5B shows a simulation result when an inner image of a nuclear reactor is generated using a displacement method of a prior art.

FIG. 5A illustrates a simulation result when an image of the interior of a nuclear reactor is generated according to the present embodiment. As a comparative example, FIG. 5B illustrates a simulation result when an image the interior of a nuclear reactor is generated using a displacement method of a prior art.

Here, a simulation is performed using a Monte Carlo code GEANT4 to create a model in which a molten fuel having a diameter of 60 cm exists at the bottom of a nuclear reactor pressure container. The calculation conditions are the same in both the embodiment and comparative example.

It is seen from FIG. 5A that by generating an image using two components of track displacement and mean energy, higher resolution is achieved than in image generation according to a conventional displacement method.

The aforementioned inner image generating apparatus identifies the position of existence of matter using the product of track displacement and mean energy of muons entering a structure, and can thereby generate an inner image of the structure with high resolution.

Although an embodiment of the present invention has been described, the present embodiment has been presented as an example and is not intended to limit the scope of the invention. This novel embodiment can be implemented in various other modes and various omissions, replacements or alterations can be made without departing from the spirit and scope of the present invention. The embodiment and modifications thereof are included in the scope and spirit of the present invention and also included in the invention described in the scope of the appended claims and within the range of equivalency thereof. It should be noted that the present embodiment can also use cosmic radiation having high energy of several hundreds of MeV to GeV or higher instead of muons.

What is claimed is:
1. An inner image generating apparatus, comprising:
a first receiver configured to receive an inlet track information and a first passage time of a muon at a first track detector provided outside of a structure;
a second receiver configured to receive an outlet track information and a second passage time of the muon at a second track detector provided outside of the structure at an opposite side of the first track detector;
a displacement calculator configured to calculate a track displacement of a track of the muon passing the structure based on the inlet track information and the outlet track information of the muon;
a mean energy calculator configured to calculate a mean energy of the muon based on a time-difference between the first passage time and the second passage time;
a data integration circuit configured to integrate a product of the track displacement and the mean energy of the muon on a projected plane assumed inside the structure, wherein each of the product is configured to be allocated at a corresponding position of the muon passing at the projected plane; and, an image generating circuit configured to generate an inner image of the structure by identifying a position of matter at the projected plane based on an integrated product obtained at the data integration circuit.

2. The inner image generating apparatus according to claim 1, wherein the image generating circuit is configured to identify an atomic number of the matter based on a relationship between the multiplied data and a radiation length of the matter.

3. The inner image generating apparatus according to claim 1, further comprising:

an identifying counter configured to pick up and identify the inlet track information received at the first receiver and the outlet track information received at the second receiver in a predetermined time period as the track of the muon passing the structure.

4. An inner image generating method, comprising:

receiving an inlet track information and a first passage time of a muon at a first track detector provided outside of a structure;

receiving an outlet track information and a second passage time of the muon at a second track detector provided outside of the structure at an opposite side of the first track detector;

calculating a track displacement of a track of the muon passing the structure based on the inlet track information and the outlet track information of the muon;

calculating a mean energy of the muon based on a time-difference between the first passage time and the second passage time;

integrating a product of the track displacement and the mean energy of the muon on a projected plane assumed inside the structure, wherein each of the product is allocated at a corresponding position of the muon passing at the projected plane; and, generating an inner image of the structure by identifying a position of matter at the projected plane based on the product integrated.

* * * * *